US009447396B2

(12) United States Patent
Ogawa et al.

(10) Patent No.: US 9,447,396 B2
(45) Date of Patent: Sep. 20, 2016

(54) METHOD FOR ACCUMULATING PROTEIN IN PLANT CELLS

(75) Inventors: Yoichi Ogawa, Wako (JP); Yasuhiro Kondo, Wako (JP); Ikuko Nishimura, Kyoto (JP); Makoto Shirakawa, Kyoto (JP); Haruko Ueda, Kyoto (JP); Tomoo Shimada, Kyoto (JP)

(73) Assignee: HONDA MOTOR CO., LTD., Tokyo (JP)

( * ) Notice: Subject to any disclaimer, the term of this patent is extended or adjusted under 35 U.S.C. 154(b) by 202 days.

(21) Appl. No.: 14/003,278

(22) PCT Filed: Feb. 24, 2012

(86) PCT No.: PCT/JP2012/054569
§ 371 (c)(1),
(2), (4) Date: Sep. 5, 2013

(87) PCT Pub. No.: WO2012/121029
PCT Pub. Date: Sep. 13, 2012

(65) Prior Publication Data
US 2013/0347145 A1    Dec. 26, 2013

(30) Foreign Application Priority Data
Mar. 9, 2011  (JP) .................................. 2011-051528

(51) Int. Cl.
| | | |
|---|---|---|
| C12N 15/82 | (2006.01) | |
| C12N 15/56 | (2006.01) | |
| C07K 14/415 | (2006.01) | |
| C12N 9/24 | (2006.01) | |
| C12N 9/26 | (2006.01) | |

(52) U.S. Cl.
CPC ........... *C12N 9/2405* (2013.01); *C12N 9/2408* (2013.01); *C12N 15/8221* (2013.01); *C12Y 302/01147* (2013.01); *C07K 2319/01* (2013.01)

(58) Field of Classification Search
None
See application file for complete search history.

(56) References Cited

FOREIGN PATENT DOCUMENTS

JP         2010-525806 A    7/2010
WO    WO 2008/132743 A2    11/2008

OTHER PUBLICATIONS

Ueda et al. (Plant Cell Physiol. 47(1): 164-175 (2006)).*
Barth et al. (The Plant Journal (2006) 46, 549-562).*
Marty (The Plant Cell, vol. 11, 587-599, Apr. 1999).*
International Search Report dated Mar. 19, 2012 corresponding to International Patent Application No. PCT/JP2012/054569 and English translation thereof.
Twyman, et al., "Molecular Farming in Plants: Host Systems and Expression Technology," Trends Biotechnology, vol. 21, No. 12, Dec. 2003, pp. 570-578.
Verma, et al., "Chloroplast Vector Systems for Biotechnology Applications," Plant Physiology, Dec. 2007, 145(4): pp. 1129-1143.
Hood, et al., "Subcellular Targeting is a Key Condition for High-Level Accumulation of Cellulase Protein in Transgenic Maize Seed," Plant Biotechnology Journal, 2007, 5(6): pp. 709-19.
Francis Marty, "Plant Vacuoles," Plant Cell., Apr. 1999, 11(4): pp. 587-600.
Dai, et al., "Improved Plant-Based Production of E1 Endoglucanase Using Potato: Expression Optimization and Tissue Targeting," Molecular Breeding, 2000, 6: pp. 277-285.
Rask, et al., "Myrosinase: Gene Family Evolution and Herbivore Defense in Brassicaceae," Plant Molecular Biology, 2000, 42(1): pp. 93-113.
Ohtonno, et al., "Identification of an Allele of VAM3/SYP22 that Confers a Semi-Dwarf Phenotype in Arabidopsis Thaliana," Plant Cell Physiol., 2005, 46(8): pp. 1358-65.
Ueda, et al., "AtVAM3 is Required for Normal Specification of Idioblasts, Myrosin Cells," Plant Cell Physiol., 2006, 47 (1): pp. 164-75.
Barth, et al., "Arabidopsis Myrosinases TGG1 and TGG2 Have Redundant Function in Glucosinolate Breakdown and Insect Defense," Plant Journal, 2006, 46(4): pp. 549-62.
Cornelissen, et al., "Structure for Tobacco Genes Encoding Pathogenesis-Related Proteins from the PR-1 Group," Nucleic Acids Research, 1987, 15(17): pp. 6799-6811.
Shimada, et al., "A Pumpkin 72-kDa Membrane Protein of Precursor-Accumulating Vesicles Has Characteristics of a Vacuolar Sorting Receptor," Plant Cell Physiol., 1997, 38(12): pp. 1414-1420.
Chen, et al., "A Gateway-Based Platform for Multigene Plant Transformation," Plant Mol. Biol., 2006, 62(6): pp. 927-936.
Kawazu, et al., "Expression of a Bacterial Endoglucanase Gene in Tobacco Increases Digestibility of Its Cell Wall Fibers," 1999, Journal of Bioscience and Bioengineering, vol. 88, No. 4, pp. 421-425.
Kimura, et al., "Molecular Breeding of Transgenic Rice Expressing a Xylanase Domain of the xynA Gene from Clostridium Thermocellum," Applied Microbiology and Biotechnology, 2003, 62: pp. 374-379.
Ziegler, et al., "Accumulation of a Thermostable Endo-1,4-β-D-glucanase in the Apoplast of Arabidopsis Thaliana Leaves," Molecular Breeding, 2000, 6: pp. 37-46.

(Continued)

*Primary Examiner* — Anne Kubelik
*Assistant Examiner* — Charles Logsdon
(74) *Attorney, Agent, or Firm* — Squire Patton Boggs (US) LLP

(57) ABSTRACT

According to the present invention, a method for stably accumulating a target protein in plant cells or a plant body, and a transgenic plant in which protein has accumulated, are provided. The method of the present invention is a method for accumulating protein in plant cells, comprising accumulating a target protein or a protein deficient in an N-terminal region of the target protein in vacuoles of myrosin cells present in a multiple mutant, in which myrosin cells deficient in intravacuolar protein are also present in a plant body at locations other than around vascular bundles, by expressing a gene that encodes a target protein having an intracellular membrane system localization signal on the N-terminal and a vacuole localization signal on the C-terminal in the multiple mutant.

2 Claims, 4 Drawing Sheets

(56) References Cited

OTHER PUBLICATIONS

Tucker, et al., "Ultra-Thermostable Cellulases from Acidothermus Cellulolyticus: Comparison of Temperature Optima with Previously Reported Cellulases," Nature Biotechnology, Aug. 1989, vol. 7: pp. 817-820.
Kengen, et al., "Puriciation and Characterization of an Extremely Thermostable β-glucosidase from the Hyperthermophilic Archaeon Pyrococcus Furiosus," Eur. J. Biochem., 1993, 213: pp. 305-312.
Nakagawa, et al., "Development of R4 Gateway Binary Vectors (R4pGWB) Enabling High-Throughput Promoter Swapping for Plant Research," Biosci. Biotechnol. Biochem., 2008, 72(2): pp. 624-629.
Van Larabeke, et al., "Large Plasmid in Agrobacterium Tumefaciens Essential for Crown Gall-Inducing Ability," Nature, Nov. 8, 1974, 252(5479): pp. 169-170.
Bechtold, et al., "In Planta Agrobacterium-Mediated Transformation of Adult Arabidopsis Thaliana Plants by Vacuum Infiltration," Methods in Molecular Biology, 1998, 82: pp. 259-266.
Ziegelhoffer, et al., "Dramatic Effects of Truncation and Sub-Cellular Targeting on the Accumulation of Recombinant Microbial Cellulase in Tobacco," Molecular Breeding, 2000, 8: pp. 147-158.
Tomoo Shimada et al., "The roles of membrane trafficking to vacuoles in Arabidopsis," Journal of Japanese Biochemical Society, 2009, Shoroku CD, p. ROMBUNNO2.S14A-3.
Thangsad, Op et al., "Cell specific, cross-species expression of myrosinases in Brassica napus, Arabidopsis thaliana and Nicotiana tabacum," Plant Molecular Biology, Mar. 2004, vol. 54(4), pp. 597-611.
Cornelissen, et al., "Structure of Tobacco Genes Encoding Pathogenesis-Related Proteins from the PR-1 Group," Nucleic Acids Research, 1987, 15(17): pp. 6799-6811.
Kengen, et al., "Purification and Characterization of an Extremely Thermostable 3-glucosidase from the Hyperthermophilic Archaeon Pyrococcus Furiosus," Eur. J. Biochem., 1993, 213: pp. 305-312.
Ziegelhoffer, et al., "Dramatic Effects of Truncation and Sub-Cellular Targeting on the Accumulation of Recombinant Microbial Cellulase in Tobacco," Molecular Breeding, 2001, 8: pp. 147-158.
Thangstad, Op et al., "Cell specific, cross-species expression of myrosinases in Brassica napus, Arabidopsis thaliana and Nicotiana tabacum," Plant Molecular Biology, Mar. 2004, vol. 54(4), pp. 597-611.
Notice of Reasons for Rejection dated Apr. 14, 2015 corresponding to Japanese Patent Application No. 2011-051528 and English translation thereof.
The Plant Journal, "Vacuolar/pre-vacuolar compartment Qa-SNAREs VAM3/SYP22 and PEP12/SYP21 have interchangeable functions in Arabidopsis," Tomohiro Uemura et al., Nov. 10, 2010, vol. 64, pp. 864 to 873.

\* cited by examiner

METHOD FOR ACCUMULATING PROTEIN IN PLANT CELLS

TECHNICAL FIELD

The present invention relates to a method for accumulating protein in specific intracellular organelles of plant cells, and to a transgenic plant produced according to that method.

The present application claims priority on the basis of Japanese Patent Application No. 2011-051528, filed in Japan on Mar. 9, 2011, the contents of which are incorporated herein by reference.

BACKGROUND ART

As a result of progress made in the field of gene recombination technology, it has become possible to introduce a gene encoding a target protein into cultured cells or cells in a plant body and express the protein in those cells. In general, when expressing protein by introducing a gene into the nuclear genome of a plant, in the case of having only introduced the genetic region that encodes the target protein, the expressed protein accumulates in the cytoplasm. In addition, by introducing a gene that encodes a protein in which several amino acids referred to as a localization signal have been added to the N-terminal and C-terminal of the target protein, the expressed protein can be made to migrate to and accumulate in locations referred to as intracellular organelles, such as endoplasmic reticulum (ER), vacuoles or chloroplasts, or in an extracellular region (apoplast) (see Non-Patent Document 1). In addition, a technology is also known that consists of introducing a gene that encodes a target protein directly into a chloroplast genome, and allowing the entire process from gene expression to protein accumulation to take place within the chloroplast (see Non-Patent Document 2).

In particular, vacuoles are intracellular organelles that have the largest volume among plant cells, and are expected to serve as favorable locations for accumulation of foreign protein. A target protein can be localized in a vacuole by adding an amino acid sequence referred to as a vacuole localization signal to the N-terminal or C-terminal of the target protein. In actuality, proteins required during germination are specifically accumulated in vacuoles in seeds, and these vacuoles are referred to as protein storage vacuoles. For example, a transgenic plant is known in which foreign cellulase is accumulated in the storage vacuoles of seeds (see, for example, Non-Patent Document 3). However, since seeds only occupy a small proportion of plant biomass, there is the problem of the amount of protein being small relative to the total amount of biomass produced.

In order to produce a large amount of protein in a plant body, it is desirable to accumulate protein in vacuoles occupying a large volume in vegetative organs accounting for the majority of plant biomass, and particularly in tissues such as leaves or stems located above ground that can be harvested easily. However, proteolytic vacuoles rich in proteases are present in the cells of vegetative organs such as leaves or stems. Consequently, these vacuoles are not suitable for protein accumulation, and even if a foreign protein was localized in the vacuoles of leaves or stems using a vacuole localization signal, it would be extremely difficult to accumulate that foreign protein at high concentrations (see, for example, Non-Patent Documents 4 and 5).

On the other hand, myrosin cells are a type of atypical cell having a unique form present in plants, and these myrosin cells are present in leaves and are capable of accumulating large amounts of protein in their vacuoles. The myrosin cells present in the leaves of plants of the order Capparales, which includes the Cruciferae family, are known to specifically accumulate the vacuoles thereof a protease thought to be involved in the plant's defense against disease and harmful insects in the form of thioglucoside glucohydrolase (TGG, also known as myrosinase) (see, for example, Non-Patent Document 6). In wild thale cress plants (*Arabidopsis thaliana*) belonging to the order Capparales, Brasiccaceae family, although myrosin cells are only present in limited regions surrounding vascular bundles, *Arabidopsis thaliana* mutant vam3-4/ssm and *Arabidopsis thaliana* mutant vam3-3 have been found that have increased numbers of myrosin cells and contain accompanying increased amounts of myrosinase in those cells (see, for example, Non-Patent Documents 7 and 8). Mutant atvam3-4/ssm is a mutant in which a frame shift has occurred due to the absence of 34 bp in the 6th intron of vam3 gene, while mutant atvam3-3 is a mutant deficient in the vam3 gene. In addition, *Arabidopsis thaliana* mutants tgg1 and tgg2 are also known that are deficient in myrosinase present in the vacuoles of myrosin cells (see, for example, Non-Patent Document 9).

RELATED ART DOCUMENTS

Non-Patent Documents

Non-Patent Document 1: Twyman, et al., Trends Biotechnol., 2003, 21(12):570-578.
Non-Patent Document 2: Verma, et al., Plant Physiol., 2007, 145(4):1129-1143.
Non-Patent Document 3: Hood, et al., Plant Biotechnol. J., 2007, 5(6):709-19.
Non-Patent Document 4: Marty, Plant Cell., 1999, 11(4):587-600.
Non-Patent Document 5: Dai, et al., Molecular Breeding, 2000, 6:277-285.
Non-Patent Document 6: Rask, et al., Plant Mol. Biol., 2000, 42(1):93-113.
Non-Patent Document 7: Ohtomo, et al., Plant Cell Physiol., 2005, 46(8):1358-65.
Non-Patent Document 8: Ueda, et al., Plant Cell Physiol., 2006, 47(1):164-75.
Non-Patent Document 9: Barth, et al., Plant J., 2006, 46(4):549-62.
Non-Patent Document 10: Cornelissen, et al., Nucleic Acids Res., 1987, 15(17):6799-6811.
Non-Patent Document 11: Shimada, et al., Plant Cell Physiol., 1997, 38(12):1414-20.
Non-Patent Document 12: Chen, et al., Plant Mol. Biol., 2006, 62(6):927-936.
Non-Patent Document 13: Kawazu, et al., 1999, Journal of Bioscience and Bioengineering, 88:421-425.
Non-Patent Document 14: Kimura, et al., Applied Microbiology and Biotechnology, 2003, 62:374-379.
Non-Patent Document 15: Ziegler, et al., Mol. Breed., 2000, 6:37-46.
Non-Patent Document 16: Tucker, et al., Nature Biotechnology, 1989, 7:817-820.
Non-Patent Document 17: Kengen, et al., Eur. J. Biochem., 1993, 213:305-312.
Non-Patent Document 18: Nakagawa, et al., Biosci. Biotechnol. Biochem., 2008, 72(2):624-9.
Non-Patent Document 19: Van Larabeke, et al., Nature, 1974, 252(5479):169-70.
Non-Patent Document 20: Bechtold, et al., Methods Mol. Biol., 1998, 82:259-66.

Non-Patent Document 21: Ziegelhoffer, et al., Molecular Breeding, 2000, 8:147-158.

DISCLOSURE OF THE INVENTION

Problems to be Solved by the Invention

Tissues in which myrosin cells are formed are limited, and are the cells that are not considered to be suitable as storage organs for producing protein. In addition, since large amounts of enzymes and other endogenous proteins accumulate in myrosin cells, it is thought to be difficult to simultaneously accumulate large amounts of a target foreign protein in addition to these endogenous proteins.

An object of the present invention is to provide a method for stably accumulating a target protein in plant cells or a plant body, and a transgenic plant in which protein has been accumulated.

Means for Solving the Problems

As a result of conducting extensive studies to solve the aforementioned problems, the inventors of the present invention found that by expressing a protein to which an intracellular membrane system localization signal and vacuole localization signal have been added in a plant body in which numerous myrosin cells deficient in endogenous proteins such as TGG1 or TGG2 are present not only at sites surrounding vascular bundles but at other sites as well; the protein can be accumulated in the plant body in a state in which it is contained in myrosin cells, thereby leading to completion of the present invention.

Namely, the present invention provides the following:

(1) a method for accumulating protein in plant cells, comprising:
expressing a gene that encodes a target protein having an intracellular membrane system localization signal on the N-terminal and a vacuole localization signal on the C-terminal in a multiple mutant, in which myrosin cells deficient in intravacuolar protein are also present in a plant body at locations other than around vascular bundles;
thereby accumulating the target protein, or a protein deficient in an N-terminal region of the target protein in vacuoles of myrosin cells present in the multiple mutant;

(2) the method for accumulating protein in plant cells described in (1) above, wherein the intravacuolar protein is thioglucoside glucohydrolase (TGG);

(3) the method for accumulating protein in plant cells described in (1) or (2) above, wherein the multiple mutant is deficient in vam3 gene;

(4) the method for accumulating protein in plant cells described in any of (1) to (3) above, wherein the multiple mutant is a mutant of a plant belonging to the Brassicaceae family;

(5) the method for accumulating protein in plant cells described in any of (1) to (4) above, wherein the multiple mutant is a plant body in which tgg1 gene and/or tgg2 gene has been further deleted from mutant atvam3-3 or atvam3-4/ssm;

(6) the method for accumulating protein in plant cells described in any of (1) to (5) above, wherein the target protein is a diastatic enzyme that hydrolyzes cellulose to sugar;

(7) a multiple mutant of *Arabidopsis thaliana*, in which tgg1 gene and/or tgg2 gene is further deleted from mutant atvam3-3 or atvam3-4/ssm;

(8) a multiple mutant of *Arabidopsis thaliana* deficient in vam3 gene, tgg1 gene and tgg2 gene;

(9) a plant that is a progeny or clone of the multiple mutant of *Arabidopsis thaliana* described in (8) above;

(10) a method for accumulating protein in plant cells, comprising:
expressing a gene that encodes a target protein having an intracellular membrane system localization signal on the N-terminal and a vacuole localization signal on the C-terminal in a mutant, which is deficient in thioglucoside glucohydrolase (TGG) in vacuoles of myrosin cells;
thereby accumulating the target protein, or a protein deficient in an N-terminal region of the target protein in vacuoles of myrosin cells present in the multiple mutant;

(11) the method for accumulating protein in plant cells described in (10) above, wherein the mutant is a plant belonging to the Brassicaceae family; and

(12) the method for accumulating protein in plant cells described in (10) or (11) above, wherein the mutant is *Arabidopsis thaliana*.

Effects of the Invention

According to the method for accumulating protein in plant cells of the present invention, a target foreign protein can be accumulated in a larger number of myrosin cells.

In addition, the multiple mutant of the present invention allows a foreign protein to be accumulated comparatively stably in vacuoles in cells at sites such as leaves and stems that account for a high proportion of plant biomass.

BEST MODE FOR CARRYING OUT THE INVENTION

Figure 1:
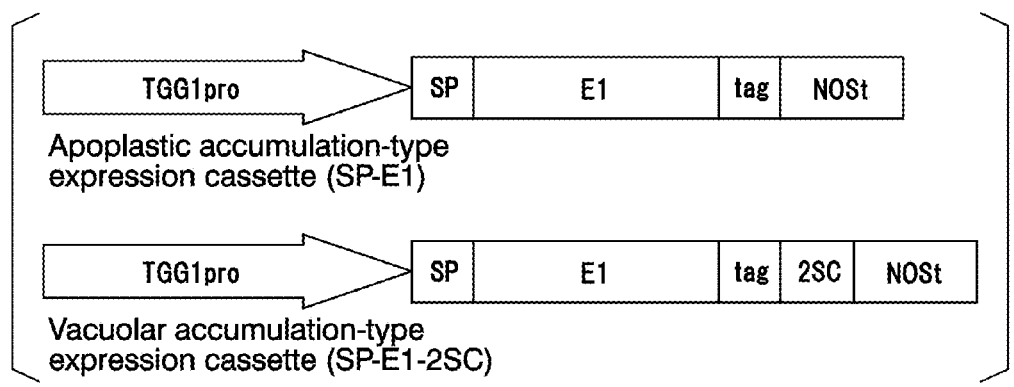
FIG. 1 is a drawing schematically showing each of the expression cassettes produced in Example 1.

The method for accumulating protein in plant cells of the present invention is characterized by using a multiple mutant, in which the number of myrosin cells has increased and which is deficient in intravacuolar protein, for the plant body in which a target gene for expressing and accumulating protein is introduced. A foreign protein can be accumulated in myrosin cells since the multiple mutant is deficient in intravacuolar protein in the myrosin cells thereof. In addition, myrosin cells of the multiple mutant are present not only around vascular bundles but also in a wide range of sites in the leaves and stems, thereby resulting in a considerable increase in the number of myrosin cells.

Consequently, target protein can be accumulated in an amount greater than that of the prior art by using myrosin cells of the multiple mutant as accumulation sites. Moreover, since the target protein is accumulated in myrosin cells, the target protein can be accumulated in plant cells while adequately reducing the effects of overexpression on the plant cells and individual plants. In other words, the multiple mutant used in the present invention allows myrosin cells in leaves and stems, in which protein accumulation was conventionally difficult, to be formed as protein storage organs.

Namely, the method for accumulating protein in plant cells of the present invention is a method for accumulating protein in plant cells, comprising expressing a gene that encodes a target protein having an intracellular membrane system localization signal on the N-terminal and a vacuole localization signal on the C-terminal in a multiple mutant, in which myrosin cells deficient in intravacuolar protein are also present in a plant body at locations other than around vascular bundles (to also be referred to as the multiple mutant of the present invention); thereby accumulating the target protein, or a protein deficient in an N-terminal region of the target protein in vacuoles of myrosin cells present in the multiple mutant.

Furthermore, in the present invention and description of the present application, a gene refers to a nucleic acid or derivative thereof that contains a base sequence that encodes a protein and by which the protein encoded thereby is synthesized by a transcription/translation mechanism provided by cells as a result of introducing the gene into cells. Genes include not only naturally-occurring genes possessed by living organisms, but also include genes artificially designed and synthesized using gene recombination technology.

There are no particular limitations on the multiple mutant of the present invention provided it inherently possesses myrosin cells. In the present invention, the multiple mutant is preferably a plant belonging to the Cruciferae family. Examples of plants of the Brassicaceae family include cabbage, Chinese cabbage, Japanese white radish, broccoli, cauliflower, thale cress, watercress, Japanese horseradish and rapeseed.

The myrosin cells of the multiple mutant of the present invention are deficient in at least one type of intravacuolar protein. The myrosin cells may be deficient in one type of intravacuolar protein or deficient in two or more types of intravacuolar proteins. Moreover, intravacuolar protein is only required to be deficient in at least one cell in the multiple mutant, and is not required to be deficient in all cells that compose the plant body of the multiple mutant. In addition, although there are no particular limitations on the deficient intravacuolar protein provided it is present in vacuoles of myrosin cells of a wild type plant body, since the effects of mutation on the entire plant body can be inhibited in compositions other than that of protein present in the vacuoles of myrosin cells, the deficient intravacuolar protein is preferably a protein specific to myrosin cells.

The intravacuolar protein that is deficient in the multiple mutant of the present invention is preferably an enzyme, and is more preferably TGG (EC3.2.1.147). By reducing the content of enzyme contained in vacuoles of myrosin cells, an expressed target protein can be accumulated more stably without being affected by endogenous protein.

For example, in the case the multiple mutant of the present invention is *Arabidopsis thaliana*, it is preferably deficient in at least one of TGG1 (At5g26000) and TGG2 (At5g25980), and is more preferably deficient in both proteins. TGG1 and TGG2 are TGG present in the vacuoles of myrosin cells of tissue of leaves and stems located above ground, and as a result of being deficient in these proteins, a target protein can be accumulated in the vacuoles of myrosin cells of leaves and stems. In addition, in *Arabidopsis thaliana*, in the case a target protein is accumulated in vacuoles of myrosin cells of the roots, it is preferably deficient in at least one of TGG4 (At1g47600) and TGG5 (At1g51470), and more preferably deficient in both of these proteins.

Myrosin cells of the multiple mutant of the present invention are also present at other sites in addition to around vascular bundles. Consequently, the myrosin cells of the multiple mutant of the present invention demonstrate an increased number of myrosin cells per plant body than those of wild strains. For example, the number of myrosin cells can be increased by deleting a gene such as vam3 gene that has an effect on myrosin cell differentiation, or by introducing a mutation that causes that gene to become dysfunctional.

In the case the multiple mutant of the present invention is *Arabidopsis thaliana*, examples of mutations that cause dysfunction of vam3 gene include a mutation that deletes 19 amino acids between an SNARE motif and a transmembrane domain in the manner of vam3 gene of the mutant atvam3-4/ssm described in Non-Patent Documents 7 and 8.

The multiple mutant of the present invention can be obtained by deleting wild vam3 gene and tgg gene, or introducing a mutation that causes dysfunction in vam3 gene and deleting tgg gene. Furthermore, gene deletion or mutant introduction can be carried out according to gene modification techniques known in the relevant technical field.

The multiple mutant of the present invention can be produced by deleting a gene that encodes intravacuolar protein present in vacuoles of myrosin cells from a mutant in which myrosin cells are present in a plant body at locations other than around vascular bundles. In addition, the multiple mutant of the present invention can also be produced by deleting vam3 gene or introducing a mutation that causes dysfunction in that gene into a mutation deficient in intravacuolar protein such as TGG. In addition, the multiple mutant can also be produced by crossing a mutant in which myrosin cells are present in a plant body at locations other than around vascular bundles with a mutant deficient in intravacuolar protein present in the vacuoles of myrosin cells, and then self-pollinating the resulting first-generation hybrids.

In the case the multiple mutant of the present invention is *Arabidopsis thaliana*, the multiple mutant can be produced by deleting tgg1 gene or tgg2 gene from mutant atvam3-3 or mutant atvam3-4/ssm described in Non-Patent Documents 7 and 8. In addition, the multiple mutant can also be produced by deleting vama3 gene from mutant attgg1tgg2 described in Non-Patent Document 9. Moreover, a multiple mutant in which myrosin cells are present not only around vascular bundles but also in a wide range of sites of the leaves and stems, and which is deficient in TGG1 and TGG2, can be produced from individual plants of second-generation hybrids by crossing mutant atvam3-3 or mutant atvam3-4/ssm with mutant atgg1tgg2 and self-pollinating the resulting first-generation hybrids.

In addition, a target protein can be accumulated in myrosin cells by expressing a gene that encodes a target protein having an intracellular membrane system localization signal on the N-terminal and a vacuole localization signal on the C-terminal in a mutant in which, although deficient in intravacuolar protein, demonstrates localization of myrosin cells similar to that of the wild strain in the manner of mutant atgg1tgg2 described in Non-Patent Document 9.

The method for accumulating protein in plant cells of the present invention comprises expressing a gene that encodes a target protein having an intracellular membrane system localization signal on the N-terminal and a vacuole localization signal on the C-terminal in the multiple mutant of the present invention. A target protein synthesized by ribosomes can be made to migrate into the ER as a result of having an intracellular membrane system localization signal on the N-terminal thereof. In addition, the target protein can be made to migrate to vacuoles as a result of having a vacuole localization signal on the C-terminal thereof.

In the present invention, there are no particular limitations on the intracellular membrane system localization signal provided by a target protein provided it is an amino acid sequence having the ability to migrate to an intracellular membrane such as ER (to be referred to as ER migration ability), and can be used by suitably selecting from signals present on the N-terminal of secretory proteins. In addition, the intracellular membrane system localization signal may also be a peptide in which one or a plurality of amino acids have been deleted, substituted or added to a known intracellular membrane system localization signal without impairing ER migration ability. A specific example of an intracellular membrane system localization signal is the intracellular membrane system localization signal possessed by tobacco mosaic virus protein Pr1a (see Non-Patent Document 10).

In the present invention, there are no particular limitations on the vacuole localization signal provided by a target protein provided it is an amino acid sequence having the ability to migrate into vacuoles, and can be used by suitably selecting from signals present on the C-terminal of proteins that migrate into vacuoles. A specific example of a vacuole localization signal is the C-terminal vacuole localization signal of pumpkin 2S albumin (2SC) (see, for example, Non-Patent Document 11).

There are some proteins accumulated in vacuoles in which at least a portion of the N-terminal intracellular membrane system localization signal has been cleaved. In the present invention as well, instead of a target protein, a target protein that is deficient in the N-terminal region of the target protein may be accumulated in myrosin cells depending on the type of intracellular membrane system localization signal provided by the target protein. Furthermore, the N-terminal cleavage site differs according to the type of target protein, and particularly the amino acid sequence of a polypeptide coupled to the intracellular membrane system localization signal. Although the deficiency results from cleavage of only the intracellular membrane system localization signal in many cases, there are also cases in which a larger N-terminal region that contains the intracellular membrane system localization signal is deleted, and cases in which only a portion of the intracellular membrane system localization signal is deleted.

In the case a target protein that accumulates in cells of the multiple mutant of the present invention is inherently provided with an intracellular membrane system localization signal or vacuole localization signal, the protein or a protein deficient in the N-terminal region of that protein can be accumulated in myrosin cells by using that protein for the target protein and expressing a gene that encodes that protein. On the other hand, in the case a target protein desired to be accumulated in cells is not provided with an intracellular membrane system localization signal or vacuole localization signal, the target protein or a protein deficient in the N-terminal region of that protein can be accumulated in myrosin cells by using a protein in which an intracellular membrane system localization system has been added to the N-terminal of that protein and a vacuole localization signal has been added to the C-terminal.

In the present invention, the target protein may also be a chimeric protein obtained by fusing a protein, in which a vacuole localization signal has been added to a target protein desired to be accumulated in cells, to the C-terminal of a protein inherently provided with an intracellular membrane system localization signal on the N-terminal thereof, either directly or through a suitable spacer.

There are no particular limitations on the method used to express and accumulate a target protein in the multiple mutant of the present invention provided it is a method that is known in the relevant technical field. For example, a plant body in which a target protein has been accumulated in vacuoles of myrosin cells (to also be referred to as a transformant of the present invention) can be produced by introducing an expression vector having a base sequence that encodes the target protein into cells of the multiple mutant of the present invention according to a method normally used in the case of producing a transgenic plant cell or transgenic plant.

An expression vector having a base sequence that encodes a target protein can be produced by incorporating DNA having a base sequence that encodes the target protein into an expression vector using commonly known gene recombination technology. A commercially available expression vector production kit may also be used.

There are no particular limitations on the expression vector provided it is an expression vector having a promoter sequence able to be transcribed in plant cells and a terminator sequence containing a polyadenylation site, and in the case of having been introduced into plant cells, is able to express a polypeptide encoded by an incorporated polynucleotide, and any arbitrary expression vector can be used that is normally used to produce a transgenic plant cell or transgenic plant. Furthermore, in the case of incorporating abase sequence that encodes a target protein in the same vector along with a base sequence that encodes another protein, it is necessary to provide an expression cassette composed of DNA having a promoter sequence, DNA having a base sequence that encodes the target protein and DNA having a terminator sequence, and an expression cassette composed of DNA having a promoter sequence, DNA having a base sequence that encodes the other protein and DNA having a terminator sequence, so that both proteins are independently expressed in cells.

Examples of expression vectors include MultiRound Gateway (see Non-Patent Document 12) entry vector and binary vectors such as pIG121 or pIG121Hm. Examples of promoters that can be used include nopaline synthase gene promoter, cauliflower mosaic virus 35S promoter and maize ubiquitin-1 (ubi1) promoter. In addition, examples of terminators that can be used include nopaline synthase gene terminator. In addition, promoters that are specific to tissue and organs may also be used. For example, an example of a leaf-specific promoter is rice rbcS promoter. The use of such tissue- or organ-specific promoters makes it possible to express a target protein in only a specific tissue or organ and not throughout the entire plant.

The expression vector is preferably an expression vector that incorporates not only DNA having a base sequence that encodes the target protein, but also other DNA such as a drug resistance gene. This is because the incorporation of other such genes facilitates the selection of plants that have been transformed by the expression vector and those that have not been transformed. Examples of drug resistance genes include kanamycin resistance gene, hygromycin resistance gene and bialaphos resistance gene.

Examples of methods used to introduce an expression vector into cells of the multiple mutant of the present invention include the *Agrobacterium* method, particle gun method, electroporation method and PEG (polyethylene glycol) method. Among these, the *Agrobacterium* method is used preferably. Furthermore, transformed cells and transformants into which an expression vector has been introduced can be selected by using drug resistance and the like as an indicator.

In addition, cultured plant cells, plant organs or plant tissue may be used for the host. Namely, plant cells in which are expressed a gene that encodes a target protein may be cells of an individual plant of the multiple mutant of the present invention, cells that have been harvested from that individual plant, cells that have been harvested and then subjected to treatment such as dedifferentiation treatment, or cultured cells that have been established from that individual plant.

By using a commonly known plant tissue culturing method and the like, an individual plant (transformant), in which a target protein or protein deficient in the N-terminal region of the target protein has accumulated in myrosin cells of the leaves or stems thereof, can be obtained from transformed cells, obtained by introducing a gene that encodes the target protein into a callus obtained by subjecting the multiple mutant of the present invention to dedifferentiation treatment. A transgenic plant can be obtained according to this plant tissue culturing method by, for example, culturing transformed plant cells using a hormone-free redifferentiation medium and cultivating by transplanting the resulting seedling plant that has formed roots in soil etc.

The transformant of the present invention in which a target protein has accumulated in the multiple mutant of the present invention can be cultivated, made into cuttings or used to obtain progeny by cross-breeding and the like in the same manner as the multiple mutant of the present invention prior to transformation. In addition, clones can also be obtained using commonly known cloning technology.

A target protein that has accumulated in vacuoles of myrosin cells, or a protein that is deficient in the N-terminal region of the target protein, can be recovered from the transformant of the present invention. There are no particular limitations on the method used to recover a target protein from the transformant of the present invention, and can be suitably selected from methods normally used in the case of extracting and purifying recombinant protein from cells or biological tissue. Examples of such methods include the method of Kawazu, et al. (see Non-Patent Document 13) and the method of Kimura, et al. (see Non-Patent Document 14).

In addition, by using a diastatic enzyme that hydrolyzes cellulose derived from plant cell wall to sugar in the manner of hyperthermophilic glucanases such as the catalytic domain of endoglucanase E1 gene derived from *Acidothermus cellulolyticus* (E1-cat) (see Non-Patent Documents 15 and 16) or the β-glucosidase gene CelB derived from *Pyrococcus furiosus* (see Non-Patent Document 17) for the target protein in the method for accumulating protein in plant cells of the present invention, a transgenic plant can be produced that serves as a preferable biomass raw material for the production of bioethanol. Since diastatic enzyme accumulates in the vacuoles of myrosin cells, the resulting transgenic plant can be cultivated in the same manner as the plant serving as host during transformation. What is more, in the case of using the transgenic plant as a biomass raw material, cellulose in the transgenic plant becomes easier to degrade as a result of the accumulated diastatic enzyme being released from the vacuoles of the myrosin cells when subjected to pretreatment for the purpose of producing bioethanol.

EXAMPLES

Although the following provides a more detailed explanation of the present invention by indicating examples thereof, the present invention is not limited to the following examples.

Example 1

Hyperthermophilic glucanase was accumulated in the vacuoles of myrosin cells of the leaves and stems of *Arabidopsis thaliana* deficient in vam3 gene, tgg1 gene and tgg2 gene.
<Production of Gene Expression Vectors>

A DNA fragment was synthesized in which tobacco mosaic virus protein signal Pr1a (see Non-Patent Document 10) was added to the 5'-end of the coding region of a region containing the catalytic domain of a diastatic enzyme in the form of endoglucanase E1 gene derived from *Acidothermus cellulolyticus* (E1-cat) (see Non-Patent Documents 15 and 16), and a tag sequence (tag) obtained by coupling an HA tag and a polyhistidine tag was added to the 3-end of the coding region. A myrosin cell-specific promoter (TGG1pro) was coupled to the DNA fragment by a ligase reaction with an *Agrobacterium* nos terminator (NOSt) on a binary vector R4pGWB401 or R4pGWB501 (see Non-Patent Document 18) to produce an apoplastic accumulation-type E1 expression cassette (SP-E1).

Similarly, a vacuolar accumulation-type E1 expression cassette (SP-E1-2SC) was produced in which pumpkin 2S albumin C-terminal vacuole localization signal (2SC) (see Non-Patent Document 11) was inserted between the tag sequence and terminal sequence of the apoplastic accumulation-type E1 expression cassette (SP-E1).

Each of the expression cassettes produced is schematically shown in FIG. 1.

A binary vector having these expression cassettes was introduced into *Agrobacterium* strain GV310 (see Non-Patent Document 19).
<Production of *Arabidopsis Thaliana* Mutant>

Mutant atvam3-4/ssm having an increased number of myrosin cells (see Non-Patent Documents 7 and 8) was crossed with mutant attgg1tgg2 deficient in TGG1 and TGG2 to obtain a multiple mutant in which the number of myrosin cells was increased and which was deficient in TGG1 and TGG2 (vam3-4/ssm×ttg1tgg2) in the vacuoles of the myrosin cells.
<Production of *Arabidopsis Thaliana* Transformant>

An atvam3-4/ssm×tgg1tgg2 mutant was grown and transformed in planta (see Non-Patent Document 20) using the aforementioned *Agrobacterium* strain retaining the binary vector.
<Immunoblot Analysis>

Leaves of the grown transformant were crushed in SDS-PAGE sample buffer to prepare a protein sample. The protein sample was transferred to a PVDF membrane after fractionating by SDS-PAGE electrophoresis. Immunoblot analysis was carried out with an ECL Western Blotting Detection System (GE Healthcare Corp.) using monoclonal antibody to an HA tag (Covance Inc.) for the primary antibody and horseradish peroxidase-labeled anti-mouse IgG antibody (GE Healthcare Corp.) for the secondary antibody.

Figure 2:
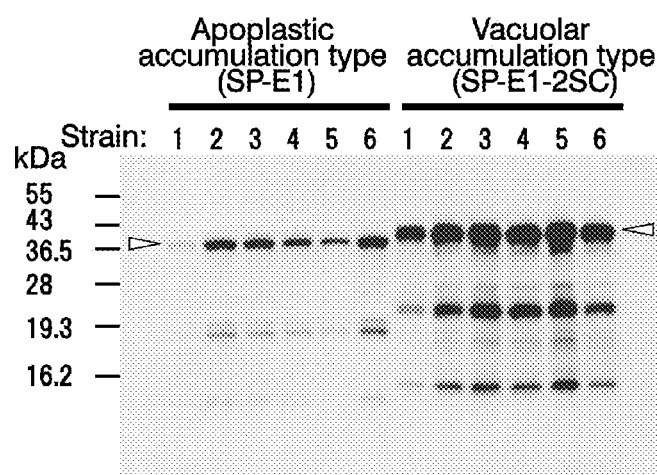
FIG. 2 is a drawing showing the results of immunoblot analysis using the anti-HA tagged antibody in Example 1 that indicates stained images of western blotting obtained with anti-HA-tagged antibody following SDS-PAGE.
Figure 3:
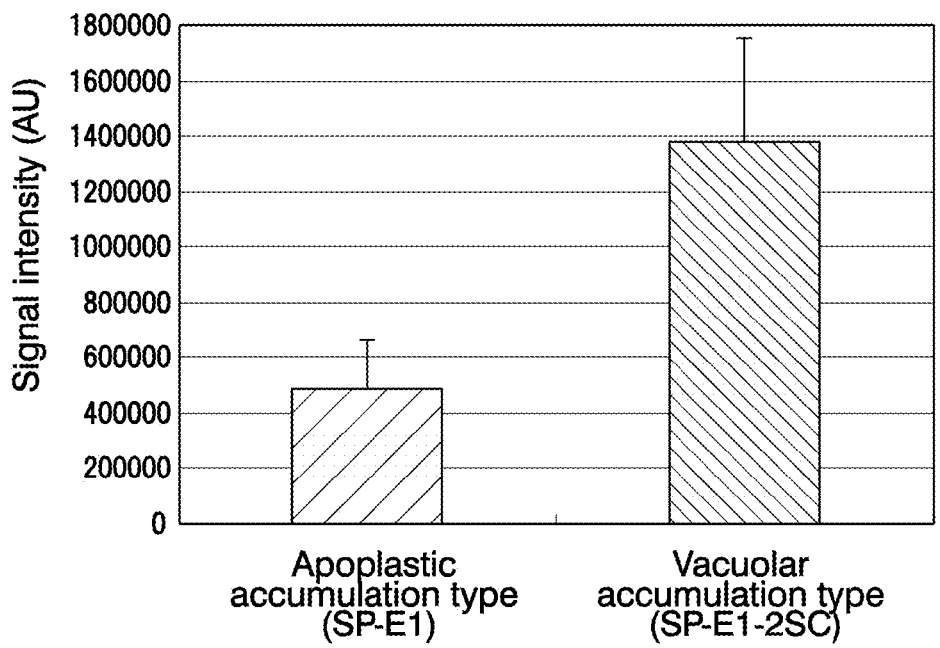
FIG. 3 is a graph showing the results of immunoblot analysis using the anti-HA-tagged antibody in Example 1 that indicates the amounts of HA-tagged fused protein present in protein samples obtained by analyzing the stained images of FIG. 2.

The results of immunoblot analysis using anti-HA-tagged antibody are shown in FIGS. 2 and 3. FIG. 2 shows western blotting stained images obtained with anti-HA-tagged antibody following SDS-PAGE. In addition, FIG. 3 indicates the amounts of HA-tagged fused protein present in the protein sample obtained (signal intensity (AU)) by analyzing the stained images of FIG. 2.

As a result, expression of HA-tagged fused protein (band indicated with arrows in FIG. 2) was confirmed in both the transformant (apoplastic accumulation type) obtained by introducing a binary vector having the apoplastic accumulation-type E1 expression cassette (SP-E1), and the transformant (vacuolar accumulation type) obtained by introducing a binary vector having the vacuolar accumulation-type E1 expression cassette (SP-E1-2SC). Namely, endoglucanase E1 protein was able to be accumulated in the vacuoles of vegetative organs for which accumulation thereof had previously been difficult. In addition, the amount of HA-tagged fused protein that accumulated in leaves was clearly greater than that in the transformant (apoplastic accumulation type). As a result, the atvam3-4/ssm×tgg1tgg2 mutant was clearly able to accumulate a large amount of foreign protein in myrosin cells. Furthermore, differences in the size of the target HA-tagged fused protein between the transformants (apoplastic accumulation type and vacuolar accumulation type) was due to the presence or absence of the pumpkin 2S albumin C-terminal vacuole localization signal (2SC).

<Enzyme Activity Assay>

Enzyme activity (nmol 4-MU/μg protein/min) was measured using 4-methylumbelliferyl β-D-cellobioside (MUC) as substrate by using all soluble protein extracted from seed-raised plants of the atvam3-4/ssm mutant (non-transformant) and transformants based on the method of Ziegelhoffer, et al. (see Non-Patent Document 21). Moreover, the ratio (accumulated concentration) of endoglucanase E1 protein to total soluble protein was calculated by comparing enzyme activities and calculated specific activities of each transformant based on a value 100% for the enzyme activity of *Streptomyces*-produced E1 (40 nmol 4-MU/μg protein/min).

Figure 4:
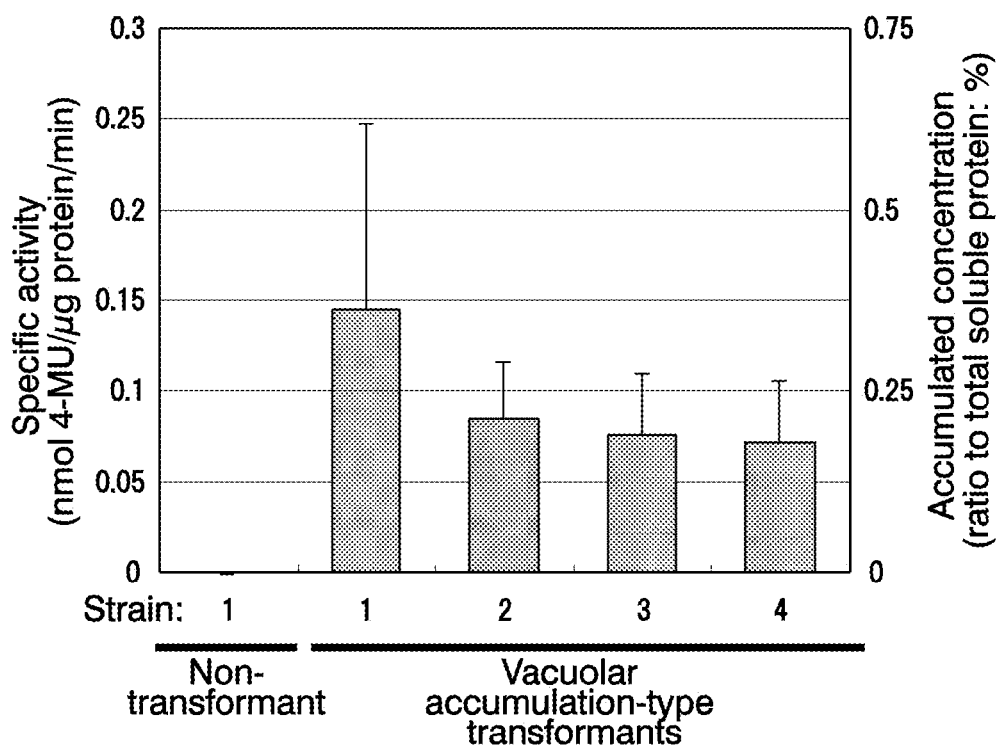
FIG. 4 is a graph showing the results of measuring enzyme activity of a non-transformant and transformants (vacuolar accumulation types) in Example 1.

The results of measuring the enzyme activities of endoglucanase E1 protein and the results of calculating the accumulated concentrations are shown in FIG. 4. There was hardly any activity observed from the non-transformant, and there was no accumulation of endoglucanase E1 protein. In contrast, in the transformant obtained by introducing a region containing the catalytic domain of endoglucanase E1 gene (E1-cat), endoglucanase activity was observed and endoglucanase E1 protein was determined to have accumulated in the plant body. In particular, in one of the four strains of transformants measured, specific activity was about 0.15 nmol 4-MU/μg protein/min, and the ratio of endoglucanase E1 protein to total soluble protein was calculated to be about 0.375%. On the basis thereof, the E1 protein that had accumulated in vacuoles of myrosin cells was indicated to retain endoglucanase activity.

Example 2

Endoglucanase E1 was introduced into wild-type *Arabidopsis thaliana* (Col-0), mutant atvam3-4/ssm having an increased number of myrosin cells, mutant attgg1tgg2 deficient in TGG1 and TGG2, and mutant atvam3-4/ssm× tgg1tgg2 produced in Example 1 followed by investigating the expression thereof and the amounts accumulated in cells.

Furthermore, the same *Agrobacterium* retaining a binary vector having the vacuolar accumulation-type E1 expression cassette (SP-E1-2SC) as that used in Example 1 was used.

More specifically, after growing each of the individual plants, the plants were transformed in planta (see Non-Patent Document 20) using *Agrobacterium* retaining a binary vector having the vacuolar accumulation-type E1 expression cassette (SP-E1-2SC) used in Example 1. Six individual plants were selected for each strain followed by carrying out immunoblot analysis on each plant.

Protein samples were prepared from leaves of the grown transformants in the same manner as Example 1, and after fractionating the proteins by SDS-PAGE electrophoresis, the proteins were transferred to a PVDF membrane followed by carrying out immunoblot analysis using anti-HA-tagged antibody.

Figure 5:
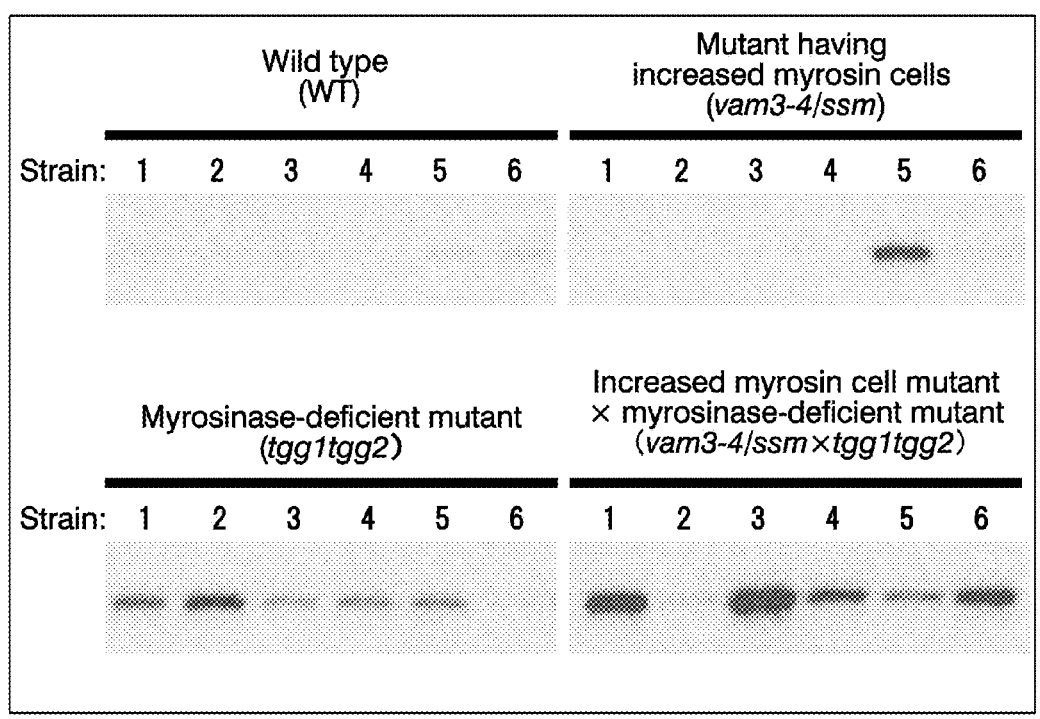
FIG. 5 is a drawing showing stained images of western blotting for each of the transformants in Example 2 using anti-HA-tagged antibody.
Figure 6:
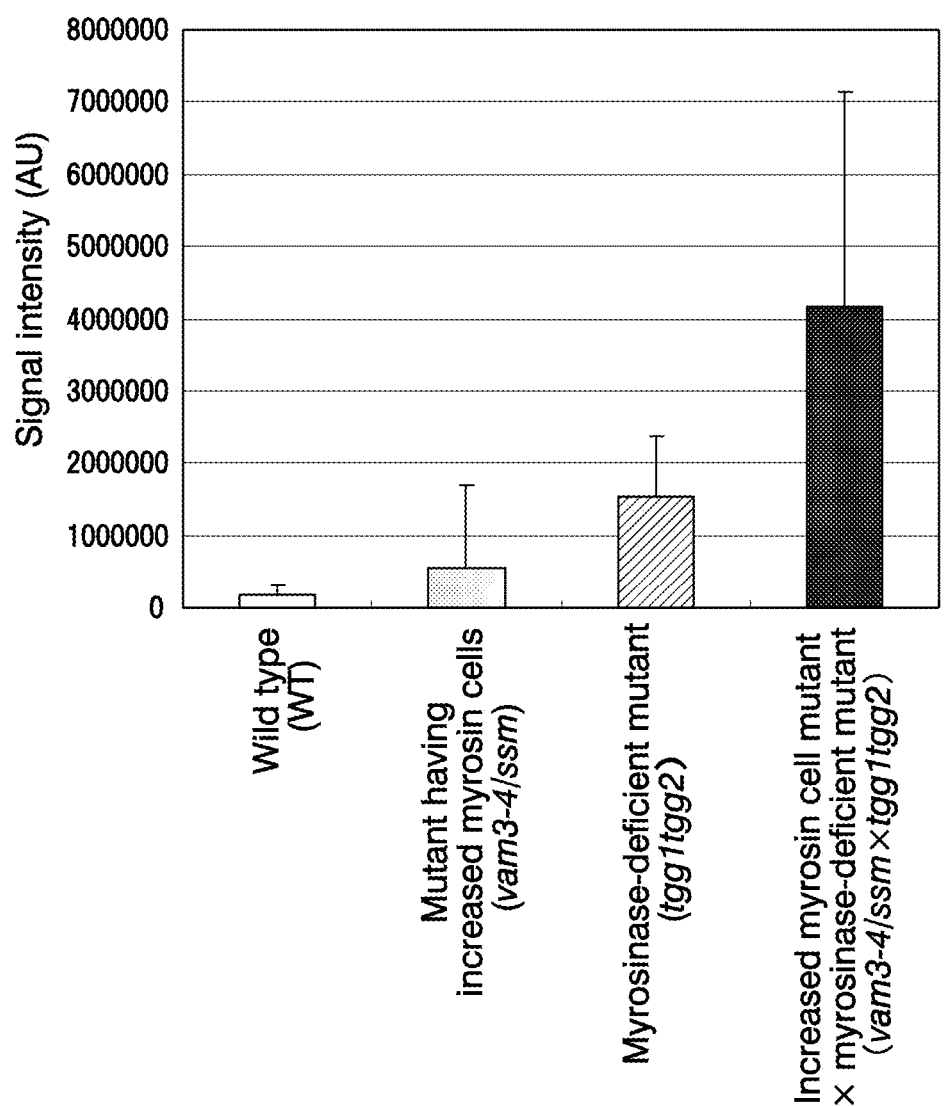
FIG. 6 is a drawing showing the results of immunoblot analysis using the anti-HA-tagged antibody in Example 2 that indicates the amounts of HA-tagged fused protein present in protein samples obtained by analyzing the stained images of FIG. 5.

The results of immunoblot analysis for each of the transformants are shown in FIGS. 5 and 6. FIG. 5 shows western blotting stained images obtained with anti-HA-tagged antibody following SDS-PAGE. In addition, FIG. 6 indicates the amounts of HA-tagged fused protein present in the protein samples obtained by analyzing the stained images of FIG. 5.

As a result, in the case of using *Arabidopsis thaliana* having wild-type myrosin cells for the host, the band of the HA-tagged fused protein (corresponding to vacuolar accumulation-type E1 protein) was thin and there was only slight accumulation of that protein. In the case of using mutant atvam3-4/ssm having an increased number of myrosin cells for the host, HA-tagged fused protein did not accumulate in the same manner as the wild-type *Arabidopsis thaliana* (Col-0) with the exception of one individual. In contrast, in the case of using mutants attgg1tgg2 and atvam3-4/ssm× tgg1tgg2 as hosts, bands corresponding to HA-tagged fused protein were clearly detected in 5 of 6 individuals.

As shown in FIG. 6, when a comparison was made of the average amounts of HA-tagged fused protein present for each strain, although there were considerable variations, the amount of HA-tagged fused protein was greater in the case of using mutant attgg1tgg2 for the host than in the case of using the wild-type *Arabidopsis thaliana* (Col-0) or mutant atvam3-4/ssm for the host, and a larger amount of E1 protein accumulated in the transformant in the case of using mutant atvam3-4/ssm×tgg1tgg2 for the host than in the case of using mutant attgg1tgg2 for the host. Namely, on the basis of these results, it was determined that it is necessary to delete intravacuolar proteins such as TGG1 or TGG2 in order to accumulate a high concentration of foreign protein in myrosin cells. In addition, the mutant atvam3-4/ssm× tgg1tgg2, having an increased number of myrosin cells, was confirmed to be able to accumulate a larger amount of foreign protein than the mutant attgg1tgg2 in which myrosin cells were limited to areas surrounding vascular bundles.

On the basis of the above results, a target protein was clearly determined to accumulate to a high concentration by expressing a gene that encodes a target protein having an intracellular membrane system localization signal on the N-terminal and a vacuole localization signal on the C-terminal in a multiple mutant in which myrosin cells deficient in intravacuolar protein are present in a plant body at locations other than the areas surrounding vascular bundles.

INDUSTRIAL APPLICABILITY

According to the method for accumulating protein in plant cells of the present invention, since a target protein can be made to accumulate in the vacuoles of myrosin cells while adequately reducing the effects of overexpression on plant cells and individual plants, this method can be used in fields such as large-volume protein production or plant genetic modification.

The invention claimed is:

1. A method for accumulating protein in plant cells, said method comprising:

transforming a plant cell with a nucleic acid encoding, in N-terminus to C-terminus order, an intracellular membrane system localization signal of tobacco mosaic virus protein Pr1a operably linked to a protein of interest operably linked to a vacuole localization signal of pumpkin 2S albumin (2SC);
   wherein the plant cell is from a plant that comprises myrosin cells, and
   wherein the plant cell contains a mutation in one or more thioglucoside glucohvdrolase (TGG) genes, thereby resulting in thioglucoside glucohvdrolase deficient myrosin cells; and
regenerating the plant cell into a plant; and
   growing the plant to allow expression of the nucleic acid and accumulation of the protein of interest, with or without the N-terminus localization signal, in the plant's myrosin cells.

2. A plant produced by the method of claim 1.

* * * * *